(12) United States Patent
Brown et al.

(10) Patent No.: US 9,259,591 B2
(45) Date of Patent: Feb. 16, 2016

(54) HOUSING FOR AN IMPLANTABLE MEDICAL DEVICE

(75) Inventors: David Brown, Lynwood, WA (US); Christopher Genau, Seattle, WA (US); Kent W. Leyde, Sammamish, WA (US); Shan Gaw, Seattle, WA (US); Jeffrey Stewart, Tacoma, WA (US)

(73) Assignee: CYBERONICS, INC., Houston, TX (US)

(*) Notice: Subject to any disclaimer, the term of this patent is extended or adjusted under 35 U.S.C. 154(b) by 0 days.

(21) Appl. No.: 12/343,386

(22) Filed: Dec. 23, 2008

(65) Prior Publication Data

US 2009/0171420 A1   Jul. 2, 2009

Related U.S. Application Data

(60) Provisional application No. 61/017,504, filed on Dec. 28, 2007.

(51) Int. Cl.
*A61N 1/378*   (2006.01)
*A61N 1/375*   (2006.01)
*A61N 1/372*   (2006.01)

(52) U.S. Cl.
CPC .............. *A61N 1/3787* (2013.01); *A61N 1/375* (2013.01); *A61N 1/3758* (2013.01); *A61N 1/37223* (2013.01)

(58) Field of Classification Search
CPC ... A61N 1/3787; A61N 1/375; A61N 1/3758; A61N 1/37223
USPC ................ 607/2, 36, 48, 60–61, 65, 115–119
See application file for complete search history.

(56) References Cited

U.S. PATENT DOCUMENTS

| | | |
|---|---|---|
| 3,218,638 A | 11/1965 | Honig |
| 3,498,287 A | 3/1970 | Ertl |

(Continued)

FOREIGN PATENT DOCUMENTS

| | | |
|---|---|---|
| CA | 2251852 | 4/1999 |
| CA | 2423840 | 2/2002 |

(Continued)

OTHER PUBLICATIONS

Adjouadi, et al. A new mathematical approach based on orthogonal operators for the detection of interictal spikes in epileptogenic data. Biomed. Sci. Instrum. 2004; 40: 175-80.

(Continued)

*Primary Examiner* — Catherine Voorhees

(57) ABSTRACT

An implantable medical device having a concave ceramic housing component; a concave metal housing component attached to the ceramic housing component to form a hermetically sealed enclosure; and an electronic trans-housing magnetic flux component disposed within the enclosure. Another aspect of the invention provides an implantable medical device having a ceramic housing component; a metal housing component; a circumferential sealing member attached to a periphery of the ceramic housing component and to a periphery of the metal housing component to form a hermetically sealed enclosure; and an electronic trans-housing magnetic flux component disposed within the enclosure. Still another aspect of the invention provides an implantable medical device with a first metal housing component; a second metal housing component, the second metal housing component forming an opening; a ceramic housing component disposed in the opening, the first metal housing component, the second metal housing component and the ceramic housing component cooperating to form a hermetically sealed enclosure; and an electronic trans-housing magnetic flux component disposed within the enclosure.

23 Claims, 5 Drawing Sheets

(56) References Cited

U.S. PATENT DOCUMENTS

| | | |
|---|---|---|
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,524,766 A | 6/1985 | Petersen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkam |
| 4,817,628 A | 4/1989 | Zealear |
| 4,821,716 A | 4/1989 | Ghajar et al. |
| 4,838,272 A | 6/1989 | Lieber |
| 4,840,617 A | 6/1989 | Osterholm et al. |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,931,056 A | 6/1990 | Ghajar et al. |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 4,998,881 A | 3/1991 | Lauks |
| 5,010,891 A | 4/1991 | Chamoun |
| 5,016,635 A | 5/1991 | Graupe |
| 5,025,807 A | 6/1991 | Zabara |
| 5,026,376 A | 6/1991 | Greenberg |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deColriolis et al. |
| 5,342,409 A | 8/1994 | Mullett |
| 5,343,064 A | 8/1994 | Spangler et al. |
| 5,346,496 A | 9/1994 | Pennig |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,634,927 A | 6/1997 | Houston et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,782,891 A * | 7/1998 | Hassler et al. .................. 607/36 |

(56) References Cited

U.S. PATENT DOCUMENTS

| | | |
|---|---|---|
| 5,792,186 A | 8/1998 | Rise |
| 5,800,474 A | 9/1998 | Bernabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |
| 5,931,791 A | 8/1999 | Saltzstein et al. |
| 5,935,128 A | 8/1999 | Carter et al. |
| 5,938,689 A | 8/1999 | Fischell et al. |
| 5,941,906 A | 8/1999 | Barreras et al. |
| 5,950,632 A | 9/1999 | Reber et al. |
| 5,954,687 A | 9/1999 | Baudino |
| 5,957,861 A | 9/1999 | Combs et al. |
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,142 A | 5/2000 | Serbousek et al. |
| 6,066,163 A | 5/2000 | John |
| 6,081,744 A | 6/2000 | Loos |
| 6,094,598 A | 7/2000 | Elsberry et al. |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,208,893 B1 | 3/2001 | Hofmann |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,283,977 B1 | 9/2001 | Ericsson et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,854 B1 | 6/2002 | Tziviskos et al. |
| 6,427,086 B1 | 7/2002 | Fischell et al. |
| 6,434,419 B1 | 8/2002 | Gevins et al. |
| 6,442,421 B1 | 8/2002 | Le Van Quyen et al. |
| 6,443,891 B1 | 9/2002 | Grevious |
| 6,453,198 B1 | 9/2002 | Torgerson |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,505,077 B1 * | 1/2003 | Kast et al. ................ 607/61 |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 | 4/2003 | Osorio et al. |
| 6,553,262 B1 | 4/2003 | Lang et al. |
| 6,560,473 B2 | 5/2003 | Dominguez |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,597,954 B1 | 7/2003 | Pless et al. |
| 6,600,956 B2 | 7/2003 | Maschino |
| 6,605,094 B1 | 8/2003 | Mann et al. |
| 6,609,020 B2 | 8/2003 | Gill |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,658,287 B1 | 12/2003 | Litt et al. |
| 6,665,562 B2 | 12/2003 | Gluckman et al. |
| 6,668,191 B1 | 12/2003 | Boveja |
| 6,671,555 B2 | 12/2003 | Gielen |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,702,818 B2 | 3/2004 | Kupferschmid et al. |
| 6,735,467 B2 | 5/2004 | Wilson |
| 6,752,812 B1 | 6/2004 | Truwit |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,879,859 B1 | 4/2005 | Boveja |
| 6,893,395 B1 | 5/2005 | Kraus et al. |
| 6,901,294 B1 | 5/2005 | Whitehurst |
| 6,901,296 B1 | 5/2005 | Whitehurst et al. |
| 6,912,419 B2 | 6/2005 | Hill |
| 6,921,538 B2 | 7/2005 | Donovan |
| 6,921,541 B2 | 7/2005 | Chasin et al. |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |
| 6,944,501 B1 | 9/2005 | Pless |
| 6,950,706 B2 | 9/2005 | Rodriquez |
| 6,973,342 B1 | 12/2005 | Swanson |
| 6,990,372 B2 | 1/2006 | Perron et al. |
| 7,010,351 B2 | 3/2006 | Firlik et al. |
| 7,033,326 B1 | 4/2006 | Pianca et al. |
| 7,089,059 B1 | 8/2006 | Pless |

(56) References Cited

U.S. PATENT DOCUMENTS

| | | |
|---|---|---|
| 7,137,969 B1 | 11/2006 | Mendez |
| 7,174,212 B1 | 2/2007 | Klehn et al. |
| 7,177,701 B1 | 2/2007 | Pianca |
| 7,212,851 B2 | 5/2007 | Donoghue et al. |
| 7,231,254 B2 | 6/2007 | DiLorenzo |
| 7,324,851 B1 | 1/2008 | DiLorenzo |
| 7,373,198 B2 | 5/2008 | Bibian et al. |
| 7,463,917 B2 | 12/2008 | Martinez |
| 7,631,015 B2 | 12/2009 | Gupta et al. |
| 7,805,196 B2 | 9/2010 | Miesel et al. |
| 7,881,798 B2 | 2/2011 | Miesel et al. |
| 8,055,348 B2 | 11/2011 | Heruth et al. |
| 8,463,393 B2 * | 6/2013 | Strother et al. ............... 607/61 |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1 | 8/2002 | Echauz et al. |
| 2002/0109621 A1 | 8/2002 | Khair et al. |
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Pless et al. |
| 2002/0177882 A1 | 11/2002 | DiLorenzo |
| 2002/0188330 A1 | 12/2002 | Gielen et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fishcell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021108 A1 * | 1/2005 | Klosterman et al. ............ 607/48 |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070810 A1 | 3/2005 | Kennedy |
| 2005/0070970 A1 | 3/2005 | Knudson et al. |
| 2005/0075067 A1 | 4/2005 | Lawson et al. |
| 2005/0075680 A1 | 4/2005 | Lowry et al. |
| 2005/0096710 A1 | 5/2005 | Kieval |
| 2005/0113885 A1 | 5/2005 | Haubrich et al. |
| 2005/0119703 A1 | 6/2005 | DiLorenzo |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0154428 A1 * | 7/2005 | Bruinsma ............... 607/60 |
| 2005/0182308 A1 | 8/2005 | Bardy |
| 2005/0182464 A1 | 8/2005 | Schulte et al. |
| 2005/0187789 A1 | 8/2005 | Hatlestad |
| 2005/0197590 A1 | 9/2005 | Osorio et al. |
| 2005/0203366 A1 | 9/2005 | Donoghue et al. |
| 2005/0203584 A1 * | 9/2005 | Twetan et al. ............... 607/36 |
| 2005/0209218 A1 | 9/2005 | Meyerson et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 * | 11/2005 | Brockway et al. ............... 607/2 |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0173259 A1 | 8/2006 | Flaherty et al. |
| 2006/0173510 A1 | 8/2006 | Besio et al. |

(56) References Cited

U.S. PATENT DOCUMENTS

| | | | |
|---|---|---|---|
| 2006/0200038 A1 | 9/2006 | Savit et al. | |
| 2006/0212092 A1 | 9/2006 | Pless et al. | |
| 2006/0212093 A1 | 9/2006 | Pless et al. | |
| 2006/0212096 A1* | 9/2006 | Stevenson | 607/60 |
| 2006/0217792 A1* | 9/2006 | Hussein et al. | 607/122 |
| 2006/0224191 A1 | 10/2006 | Dilorenzo | |
| 2006/0253096 A1 | 11/2006 | Blakley et al. | |
| 2006/0291968 A1 | 12/2006 | Greenberg | |
| 2006/0293578 A1 | 12/2006 | Rennaker, II | |
| 2006/0293720 A1 | 12/2006 | DiLorenzo et al. | |
| 2007/0027367 A1 | 2/2007 | Oliver et al. | |
| 2007/0027387 A1 | 2/2007 | Fendrock | |
| 2007/0027514 A1 | 2/2007 | Gerber | |
| 2007/0035910 A1* | 2/2007 | Stevenson | 361/302 |
| 2007/0043459 A1 | 2/2007 | Abbott, III et al. | |
| 2007/0055320 A1 | 3/2007 | Weinand | |
| 2007/0060973 A1 | 3/2007 | Ludvig et al. | |
| 2007/0073355 A1 | 3/2007 | DiLorenzo | |
| 2007/0073357 A1* | 3/2007 | Rooney et al. | 607/46 |
| 2007/0100398 A1 | 5/2007 | Sloan | |
| 2007/0142862 A1 | 6/2007 | DiLorenzo | |
| 2007/0149952 A1 | 6/2007 | Bland et al. | |
| 2007/0150024 A1 | 6/2007 | Leyde et al. | |
| 2007/0150025 A1 | 6/2007 | DiLorenzo et al. | |
| 2007/0161919 A1 | 7/2007 | DiLorenzo | |
| 2007/0162086 A1 | 7/2007 | DiLorenzo | |
| 2007/0167991 A1 | 7/2007 | DiLorenzo | |
| 2007/0185890 A1 | 8/2007 | VanEpps et al. | |
| 2007/0208212 A1 | 9/2007 | DiLorenzo | |
| 2007/0213629 A1 | 9/2007 | Greene | |
| 2007/0213785 A1 | 9/2007 | Osorio et al. | |
| 2007/0217121 A1* | 9/2007 | Fu et al. | 361/302 |
| 2007/0238939 A1 | 10/2007 | Giftakis et al. | |
| 2007/0244407 A1 | 10/2007 | Osorio | |
| 2007/0250077 A1 | 10/2007 | Skakoon et al. | |
| 2007/0250901 A1 | 10/2007 | McIntire et al. | |
| 2007/0287931 A1 | 12/2007 | DiLorenzo | |
| 2008/0021341 A1 | 1/2008 | Harris et al. | |
| 2008/0027347 A1 | 1/2008 | Harris et al. | |
| 2008/0027348 A1 | 1/2008 | Harris et al. | |
| 2008/0027515 A1 | 1/2008 | Harris et al. | |
| 2008/0033502 A1 | 2/2008 | Harris et al. | |
| 2008/0082019 A1 | 4/2008 | Ludving et al. | |
| 2008/0091090 A1 | 4/2008 | Guillory et al. | |
| 2008/0103556 A1* | 5/2008 | Li et al. | 607/61 |
| 2008/0114417 A1 | 5/2008 | Leyde | |
| 2008/0119900 A1 | 5/2008 | DiLorenzo | |
| 2008/0161712 A1 | 7/2008 | Leyde | |
| 2008/0161713 A1 | 7/2008 | Leyde et al. | |
| 2008/0183096 A1 | 7/2008 | Synder et al. | |
| 2008/0183097 A1 | 7/2008 | Leyde et al. | |
| 2008/0208074 A1 | 8/2008 | Synder et al. | |
| 2008/0221876 A1 | 9/2008 | Holdrich | |
| 2008/0234598 A1 | 9/2008 | Synder et al. | |
| 2008/0255582 A1 | 10/2008 | Harris | |
| 2008/0273287 A1* | 11/2008 | Marinkov et al. | 361/302 |
| 2008/0319281 A1 | 12/2008 | Aarts | |
| 2009/0018609 A1 | 1/2009 | DiLorenzo | |
| 2009/0062696 A1 | 3/2009 | Nathan et al. | |
| 2009/0069892 A1* | 3/2009 | Zimmerling et al. | 623/11.11 |
| 2009/0264952 A1 | 10/2009 | Jassemidis et al. | |
| 2010/0023089 A1 | 1/2010 | DiLorenzo | |
| 2011/0260855 A1 | 10/2011 | John et al. | |
| 2011/0319785 A1 | 12/2011 | Snyder et al. | |

FOREIGN PATENT DOCUMENTS

| | | |
|---|---|---|
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022 | 12/2005 |
| EP | 0124663 A1 | 11/1984 |
| EP | 0898460 | 3/1999 |
| EP | 1145735 A2 | 10/2001 |
| EP | 1145736 A2 | 10/2001 |
| EP | 1307260 | 5/2003 |
| EP | 1335668 | 8/2003 |
| EP | 1525551 | 4/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 2004/008373 A2 | 1/2004 |
| WO | WO 2004/032720 A2 | 4/2004 |
| WO | WO 2004/034231 A2 | 4/2004 |
| WO | WO 2004/034879 A2 | 4/2004 |
| WO | WO 2004/034880 A2 | 4/2004 |
| WO | WO 2004/034881 A2 | 4/2004 |
| WO | WO 2004/034882 A2 | 4/2004 |
| WO | WO 2004/034883 A2 | 4/2004 |
| WO | WO 2004/034885 A2 | 4/2004 |
| WO | WO 2004/034982 A2 | 4/2004 |
| WO | WO 2004/034997 A2 | 4/2004 |
| WO | WO 2004/034998 A2 | 4/2004 |
| WO | WO 2004/035130 A2 | 4/2004 |
| WO | WO 2004/036370 A2 | 4/2004 |
| WO | WO 2004/036372 A2 | 4/2004 |
| WO | WO 2004/036376 A2 | 4/2004 |
| WO | WO 2004/036377 A2 | 4/2004 |
| WO | WO 2004/037342 A2 | 5/2004 |
| WO | WO 2004/043536 A1 | 5/2004 |
| WO | WO 2004/091718 A1 | 10/2004 |
| WO | WO 2005/007236 A2 | 1/2005 |
| WO | WO 2005/028026 A1 | 3/2005 |
| WO | WO 2005/028028 A1 | 3/2005 |
| WO | WO 2005/031630 A2 | 4/2005 |
| WO | WO 2005/051167 A1 | 6/2005 |
| WO | WO 2005/051306 A2 | 6/2005 |
| WO | WO 2005/117693 A1 | 12/2005 |
| WO | WO 2006/014971 A2 | 2/2006 |
| WO | WO 2006/014972 A2 | 2/2006 |
| WO | WO 2006/020794 A2 | 2/2006 |

(56) References Cited

FOREIGN PATENT DOCUMENTS

| | | |
|---|---|---|
| WO | WO 2006/035392 A1 | 4/2006 |
| WO | WO 2007/150003 A2 | 12/2007 |

OTHER PUBLICATIONS

Adjouadi, et al. Detection of interictal spikes and artifactual data through orthogonal transformations. J. Clin. Neurophysiol. 2005; 22(1):53-64.
Adjouadi, et al. Interictal spike detection using the Walsh transform. IEEE Trans. Biomed. Eng. 2004; 51(5): 868-72.
Aksenova, et al. Nonparametric on-line detection of changes in signal spectral characteristics for early prediction of epilepsy seizure onset. J. Automation and Information Sciences. 2004; 36(8): 35-45.
Aksenova, et al. On-line disharmony detection for early prediction of epilepsy seizure onset. 5th International Workshop Neural Coding 2003. Aulla (Italy) Sep. 20-25, 2003. (Abstract).
Andrzejak, et al. Bivariate surrogate techniques: necessity, strengths, and caveats. Physical Review E. 2003; 68: 066202-1-066202-15.
Andrzejak, et al. Testing the null hypothesis of the nonexistence of a preseizure state. Physical Review E. 2003; 67: 010901-1-010901-4.
Aschenbrenner-Scheibe, et al. How well can epileptic seizures be predicted? An evaluation of a nonlinear method. Brain. 2003; 126: 2616-26.
Bangham et al. Diffusion of univalent ions across the lamellae of swollen phospholipids. 1965. J Mol. Biol. 13: 238-252.
Baruchi, et al. Functional holography of complex networks activity—From cultures to the human brain. Complexity. 2005; 10(3): 38 R 51.
Baruchi, et al. Functional holography of recorded neuronal networks activity. Neuroinformatics. 2004; 2(3): 333-51.
Ben-Hur, et al. Detecting stable clusters using principal component analysis. Methods Mol. Biol. 2003; 224: 159-82.
Bergey, et al. Epileptic seizures are characterized by changing signal complexity. Clin. Neurophysiol. 2001; 112(2): 241-9.
Betterton, et al. Determining State of Consciousness from the Intracranial Electroencephalogram (IEEG) for Seizure Prediction. From Proceeding (377) Modeling, Identification, and Control. 2003; 377-201: 313-317.
Bhattacharya, et al. Enhanced phase synchrony in the electroencephalograph gamma band for musicians while listening to music. Phys. Rev. E. 2001; 64:012902-1-4.
Boley, et al. Training Support Vector Machine using Adaptive Clustering. 2004 SIAM International Conference on Data Mining, Apr. 22-Apr. 24, 2004. Lake Buena Vista, FL, USA. 12 pages.
Burges, C. A Tutorial on Support Vector Machines for Pattern Recognition. Data Mining and Knowledge Discovery. 1998; 2: 121-167.
Cao, et al. Detecting dynamical changes in time series using the permutation entropy. Physical Review E. 2004; 70:046217-1-046217-7.
Carretero-Gonzalez, et al. Scaling and interleaving of subsystem Lyapunov exponents for spatio-temporal systems. Chaos. 1999; 9(2): 466-482.
Casdagli, et al. Characterizing nonlinearity in invasive EEG recordings from temporal lobe epilepsy. Physica D. 1996; 99 (2/3): 381-399.
Casdagli, et al. Nonlinear Analysis of Mesial Temporal Lobe Seizures Using a Surrogate Data Technique. Epilepsia. 1995; 36, suppl. 4, pp. 142.
Casdagli, et al. Non-linearity in invasive EEG recordings from patients with temporal lobe epilepsy. Electroencephalogr. Clin. Neurophysiol. 1997; 102(2): 98-105.
Cerf, et al. Criticality and synchrony of fluctuations in rhythmical brain activity: pretransitional effects in epileptic patients. Biol. Cybern. 2004; 90(4): 239-55.
Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.
Chaovalitwongse, et al. EEG Classification in Epilepsy. Annals. 2004; 2(37): 1-31.
Chaovalitwongse, et al. Performance of a seizure warning algorithm based on the dynamics of intracranial EEG. Epilepsy Res. 2005; 64(3): 93-113.
Chavez, et al. Spatio-temporal dynamics prior to neocortical seizures: amplitude versphase couplings. IEEE Trans. Biomed. Eng. 2003; 50(5):571-83.
Crichton, Michael, "Terminal Man", 1972, Ballantine Books, NY, NY, pp. 21-24, 32-33, 70-71, and 74-81.
D'Alessandro, et al. A multi-feature and multi-channel univariate selection process for seizure prediction. Clin. Neurophysiol. 2005; 116(3): 506-16.
D'Alessandro, et al. Epileptic seizure prediction using hybrid feature selection over multiple intracranial EEG electrode contacts: a report of four patients. IEEE Trans. Biomed. Eng. 2003; 50(5): 603-15.
Drury, et al. Seizure prediction using scalp electroencephalogram. Exp. Neurol. 2003; 184 Suppl 1: S9-18.
Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.
Ebersole, J. S. In search of seizure prediction: a critique. Clin. Neurophysiol. 2005; 116(3): 489-92.
Elbert et al. Chaos and Physiology: Deterministic Chaos in Excitable Cell Assemblies. Physiological Reviews. 1994; 74(1):1-47.
Elger, et al. Nonlinear EEG analysis and its potential role in epileptology. Epilepsia. 2000; 41 Suppl 3: S34-8.
Elger, et al. Seizure prediction by non-linear time series analysis of brain electrical activity. Eur. J. Neurosci. 1998; 10(2): 786-789.
Esteller, et al. A Comparison of Waveform Fractal Dimension Algorithms. IEEE Transactions on Circuits and Systems. 2001; vol. 48(2): 177-183.
Esteller, et al. Continuoenergy variation during the seizure cycle: towards an on-line accumulated energy. Clin. Neurophysiol. 2005; 116(3): 517-26.
Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.
Faul, et al. An evaluation of automated neonatal seizure detection methods. Clin. Neurophysiol. 2005; 116(7): 1533-41.
Fein, et al. Common reference coherence data are confounded by power and phase effects. Electroencephalogr. Clin. Neurophysiol. 1988; 69:581-584.
Fell, et al. Linear inverse filtering improves spatial separation of nonlinear brain dynamics: a simulation study. J. Neurosci. Methods. 2000; 98(1): 49-56.
Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.
Fisher et al. 1999. Reassessment: Vagnerve stimulation for epilepsy, A report of the therapeutics and technology assessment subcommittee of the American Academy of Neurology. Neurology.53: 666-669.
Franaszczuk et al.; An autoregressive method for the measurement of synchronization of interictal and ictal EEG signals; Biological Cybernetics, vol. 81; No. 1; pp. 3-9; 1999.
Gardner, A. B. A Novelty Detection Approach to Seizure Analysis from Intracranial EEG. Georgia Institute of Technology. Apr. 2004. A dissertation available at http://etd.gatech.edu/theses /available/etd-04122004-132404/unrestricted/gardner_andrew_b_200405_phd.pdf. Accessed Feb. 28, 2006.
Geva, et al. Forecasting generalized epileptic seizures from the EEG signal by wavelet analysis and dynamic unsupervised fuzzy clustering. IEEE Trans. Biomed. Eng. 1998; 45(10): 1205-16.
Gigola, et al. Prediction of epileptic seizures using accumulated energy in a multiresolution framework. J. Neurosci. Methods. 2004; 138(1-2): 107-111.
Guyon, I. An introduction to variable and feature selection. Journal of Machine Learning Research. 2003; 3:1157-1182.

(56) References Cited

OTHER PUBLICATIONS

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.
Harrison, et al. Accumulated energy revised. Clin. Neurophysiol. 2005; 116(3):527-31.
Harrison, et al. Correlation dimension and integral do not predict epileptic seizures. Chaos. 2005; 15(3): 33106-1-15.
Hearst M. Trends & Controversies: Support Vector Machines. IEEE Intelligent Systems. 1998; 13: 18-28.
Hively, et al. Channel-consistent forewarning of epileptic events from scalp EEG. IEEE Trans. Biomed. Eng. 2003; 50(5): 584-93.
Hively, et al. Detecting dynamical changes in nonlinear time series. Physics Letters A. 1999; 258: 103-114.
Hively, et al. Epileptic Seizure Forewarning by Nonlinear Techniques. ORNL/TM-2000/333 Oak Ridge National Laboratory. Nov. 2000. Available at http://computing.oml.gov/cse_home/staff/hively/NBICradaAnnualRpt FY00.pdf. Accessed Feb. 28, 2006.
Hjorth, B. Source derivation simplifies topographical EEG interpretation. Am. J. EEG Technol. 1980; 20: 121-132.
Hsu, et al. A practical guide to support vector classification. Technical report, Department of Computer Science and Information Technology, National Taiwan University, 2003. Available at http://www.csie.ntu.edu.tw/~cjlin/papers/guide/guide.pdf. Accessed Feb. 28, 2006.
Huynh, J. A. Evaluation of Gene Selection Using Support Vector Machine Recursive Feature Elimination. Arizona State University. May 26, 2004. (28 pages).
Huynh, J. A. Evaluation of Gene Selection Using Support Vector Machine Recursive Feature Elimination. Presentation slides. (41 pages) (May 26, 2004).
Iasemidis, et al. Adaptive epileptic seizure prediction system. IEEE Trans. Biomed. Eng. 2003; 50(5):616-27.
Iasemidis, et al. Automated Seizure Prediction Paradigm. Epilepsia. 1998; vol. 39, pp. 56.
Iasemidis, et al. Chaos Theory and Epilepsy. The Neuroscientist. 1996; 2:118-126.
Iasemidis, et al. Comment on "Inability of Lyapunov exponents to predict epileptic seizures." Physical Review Letters. 2005; 94(1):019801-1.
Iasemidis, et al. Detection of the Preictal Transition State in Scalp-Sphenoidal EEG Recordings. American Clinical Neurophysiology Society Annual Meeting, Sep. 1996. pp. C206.
Iasemidis, et al. Dynamical Interaction of the Epileptogenic Focwith Extrafocal Sites in Temporal Lobe Epilepsy (TLE). Ann. Neurol. 1997; 42, pp. 429. pp. M146.
Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.
Iasemidis, et al. Localizing Preictal Temporal Lobe Spike Foci Using Phase Space Analysis. Electroencephalography and Clinical Neurophysiology. 1990; 75, pp. S63-S64.
Iasemidis, et al. Long-term prospective on-line real-time seizure prediction. Clin. Neurophysiol. 2005; 116(3):532-44.
Iasemidis, et al. Long-Time-Scale Temporo-spatial Patterns of Entrainment of Preictal Electrocorticographic Data in Human Temporal Lobe Epilepsy. Epilepsia. 1990; 31(5):621.
Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.
Iasemidis, et al. Modelling of ECoG in temporal lobe epilepsy. Biomed. Sci. Instrum. 1988; 24: 187-93.
Iasemidis, et al. Nonlinear Dynamics of EcoG Data in Temporal Lobe Epilepsy. Electroencephalography and Clinical Neurophysiology. 1998; 5, pp. 339.
Iasemidis, et al. Phase space topography and the Lyapunov exponent of electrocorticograms in partial seizures. Brain Topogr. 1990; 2(3): 187-201.
Iasemidis, et al. Preictal Entrainment of a Critical Cortical Mass is a Necessary Condition for Seizure Occurrence. Epilepsia. 1996; 37, suppl. 5. pp. 90.
Iasemidis, et al. Preictal-Postictal Versus Postictal Analysis for Epileptogenic Focus Localization. J. Clin. Neurophysiol. 1997; 14, pp. 144.
Iasemidis, et al. Quadratic binary programming and dynamic system approach to determine the predictability of epileptic seizures. Journal of Combinatorial Optimization. 2001; 5: 9-26.
Iasemidis, et al. Quantification of Hidden Time Dependencies in the EEG within the Framework of Non-Linear Dynamics. World Scientific. 1993; pp. 30-47.
Iasemidis, et al. Spatiotemporal dynamics of human epileptic seizures. World Scientific. 1996; pp. 26-30.
Iasemidis, et al. Spatiotemporal Evolution of Dynamical Measures Precedes Onset of Mesial Temporal Lobe Seizures. Epilepsia. 1994; 358, pp. 133.
Iasemidis, et al. Spatiotemporal Transition to Epileptic Seizures: A Nonlinear Dynamical Analysis of Scalp and Intracranial EEG Recordings. (In SILVA, F.L. Spatiotemporal Models in Biological and Artificial Systems. Ohmsha IOS Press. 1997; 37, pp. 81-88.).
Iasemidis, et al. The evolution with time of the spatial distribution of the largest Lyapunov exponent on the human epileptic cortex. World Scientific. 1991; pp. 49-82.
Iasemidis, et al. The Use of Dynamical Analysis of EEG Frequency Content in Seizure Prediction. American Electroencephalographic Society Annual Meeting, Oct. 1993.
Iasemidis, et al. Time Dependencies in Partial Epilepsy. 1993; 34, pp. 130-131.
Iasemidis, et al. Time dependencies in the occurrences of epileptic seizures. Epilepsy Res. 1994; 17(1): 81-94.
Iasemidis, L. D. Epileptic seizure prediction and control. IEEE Trans. Biomed. Eng. 2003; 50(5):549-58.
Jerger, et al. Early seizure detection. Journal of Clin. Neurophysiol. 2001; 18(3):259-68.
Jerger, et al. Multivariate linear discrimination of seizures. Clin. Neurophysiol. 2005; 116(3):545-51.
Jouny, et al. Characterization of epileptic seizure dynamics using Gabor atom density. Clin. Neurophysiol. 2003; 114(3):426-37.
Jouny, et al. Signal complexity and synchrony of epileptic seizures: is there an identifiable preictal period? Clin. Neurophysiol. 2005; 116(3):552-8.
Kapiris, et al. Similarities in precursory features in seismic shocks and epileptic seizures. Europhys. Lett. 2005; 69(4):657-663.
Katz, et al. Does interictal spiking change prior to seizures? Electroencephalogr. Clin. Neurophysiol. 1991; 79(2):153-6.
Kerem, et al. Forecasting epilepsy from the heart rate signal. Med. Biol. Eng. Comput. 2005; 43(2):230-9.
Khalilov, et al. Epileptogenic actions of GABA and fast oscillations in the developing hippocampus. Neuron. 2005; 48(5):787-96.
Korn, et al. Is there chaos in the brain? II. Experimental evidence and related models. C. R. Biol. 2003; 326(9):787-840.
Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006 (106 pp).
Kreuz, et al. Measure profile surrogates: a method to validate the performance of epileptic seizure prediction algorithms. Phys. Rev. E. 2004; 69(6 Pt 1):061915-1-9.
Lachaux, et al. Measuring phase synchrony in brain signals. Hum. Brain Mapp. 1999; 8(4):194-208.
Lai, et al. Controlled test for predictive power of Lyapunov exponents: their inability to predict epileptic seizures. Chaos. 2004; 14(3):630-42.
Lai, et al. Inability of Lyapunov exponents to predict epileptic seizures. Phys. Rev. Lett. 2003; 91(6):068102-1-4.
Latka, et al. Wavelet analysis of epileptic spikes. Phys. Rev. E. 2003; 67(5 Pt 1):052902 (6 pages).
Le Van Quyen, et al. Anticipating epileptic seizures in real time by a non-linear analysis of similarity between EEG recordings. Neuroreport. 1999; 10(10):2149-55.
Le Van Quyen, et al. Author's second reply. The Lancet. 2003; 361:971.

(56) References Cited

OTHER PUBLICATIONS

Le Van Quyen, et al. Comparison of Hilbert transform and wavelet methods for the analysis of neuronal synchrony. J. Neurosci. Methods. 2001; 111(2):83-98.
Le Van Quyen, et al. Nonlinear analyses of interictal EEG map the brain interdependences in human focal epilepsy. Physica D. 1999; 127:250-266.
Le Van Quyen, et al. Preictal state identification by synchronization changes in long-term intracranial EEG recordings. Clin. Neurophysiol. 2005; 116(3):559-68.
Le Van Quyen, M. Anticipating epileptic seizures: from mathematics to clinical applications. C. R. Biol. 2005; 328(2):187-98.
Lehnertz, et al. Nonlinear EEG analysis in epilepsy: its possible use for interictal focus localization, seizure anticipation, and prevention. J. Clin. Neurophysiol. 2001; 18(3):209-22.
Lehnertz, et al. Seizure prediction by nonlinear EEG analysis. IEEE Eng. Med. Biol. Mag. 2003; 22(1):57-63.
Lehnertz, et al. The First International Collaborative Workshop on Seizure Prediction: summary and data description. Clin. Neurophysiol. 2005; 116(3):493-505.
Lehnertz, K. Non-linear time series analysis of intracranial EEG recordings in patients with epilepsy—an overview. Int. J. Psychophysiol. 1999; 34(1):45-52.
Lemos, et al. The weighted average reference montage. Electroencephalogr. Clin. Neurophysiol. 1991; 79(5):361-70.
Li, et al. Fractal spectral analysis of pre-epileptic seizures in terms of criticality. J. Neural Eng. 2005; 2(2):11-16.
Li, et al. Linear and nonlinear measures and seizure anticipation in temporal lobe epilepsy. J. Comput. Neurosci. 2003; 15(3):335-45.
Li, et al. Non-linear, non-invasive method for seizure anticipation in focal epilepsy. Math. Biosci. 2003; 186(1):63-77.
Litt, et al. Prediction of epileptic seizures. Lancet Neurol. 2002; 1(1):22-30.
Litt, et al. Seizure prediction and the preseizure period. Curr. Opin. Neurol. 2002; 15(2):173-7.
Maiwald, et al. Comparison of three nonlinear seizure prediction methods by means of the seizure prediction characteristic. Physica D. 2004; 194:357-368.
Mangasarian, et al. Lagrangian Support Vector Machines. Journal of Machine Learning Research. 2001; 1:161-177.
Martinerie, et al. Epileptic seizures can be anticipated by non-linear analysis. Nat. Med. 1998; 4(10):1173-6.
McSharry, et al. Comparison of predictability of epileptic seizures by a linear and a nonlinear method. IEEE Trans. Biomed. Eng. 2003; 50(5):628-33.
McSharry, et al. Linear and non-linear methods for automatic seizure detection in scalp electro-encephalogram recordings. Med. Biol. Eng. Comput. 2002; 40(4):447-61.
McSharry, P. E. Detection of dynamical transitions in biomedical signals using nonlinear methods. Lecture Notes in Computer Science 2004; 3215:483-490.
Meng, et al. Gaussian mixture models of ECoG signal features for improved detection of epileptic seizures. Med. Eng. Phys. 2004; 26(5):379-93.
Mizuno-Matsumoto, et al. Wavelet-crosscorrelation analysis can help predict whether bursts of pulse stimulation will terminate after discharges. Clin. Neurophysiol. 2002; 113(1):33-42.
Mormann et al.; Seizure prediction: the long and winding road; Brain; vol. 130; No. 2; pp. 314-333; Sep. 28, 2006.
Mormann, et al. Automated detection of a preseizure state based on a decrease in synchronization in intracranial electroencephalogram recordings from epilepsy patients. Phys. Rev. E. 2003; 67(2 Pt 1):021912-1-10.
Mormann, et al. Epileptic seizures are preceded by a decrease in synchronization. Epilepsy Res. 2003; 53(3):173-85.
Mormann, et al. Mean phase coherence as a measure for phase synchronization and its application to the EEG of epilepsy patients. Physica D. 2000; 144:358-369.
Mormann, et al. On the predictability of epileptic seizures. Clin. Neurophysiol. 2005; 116(3):569-87.
Mormann, et al. Seizure anticipation: from algorithms to clinical practice. Curr. Opin. Neurol. 2006; 19(2):187-93.
Navarro, et al. Seizure anticipation in human neocortical partial epilepsy. Brain. 2002; 125:640-55.
Navarro, et al. Seizure anticipation: do mathematical measures correlate with video—EEG evaluation? Epilepsia. 2005; 46(3):385-96.
Niederhauser, et al. Detection of seizure precursors from depth—EEG using a sign periodogram transform. IEEE Trans. Biomed. Eng. 2003; 50(4):449-58.
Nigam, et al. A neural-network-based detection of epilepsy. Neurological Research. 2004; 26(1):55-60.
Osorio, et al. Automated seizure abatement in humans using electrical stimulation. Ann. Neurol. 2005; 57(2):258-68.
Osorio, et al. Performance reassessment of a real-time seizure-detection algorithm on long ECoG series. Epilepsia. 2002; 43(12):1522-35.
Osorio, et al. Real-time automated detection and quantitative analysis of seizures and short-term prediction of clinical onset. Epilepsia. 1998; 39(6):615-27.
Ossadtchi, et al. Hidden Markov modelling of spike propagation from interictal MEG data. Phys. Med. Biol. 2005; 50(14):3447-69.
Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.
Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.
Platt, et al. Large Margin DAGs for Multiclass Classification. S.A. Solla. T.K. Leen adn K. R. Muller (eds.). 2000; pp. 547-553.
Platt, J. C. Using Analytic QP and Sparseness to Speed Training of Support Vector Machines. Advances in Neural Information Processing Systems. 1999; 11:557-563.
Protopopescu, et al. Epileptic event forewarning from scalp EEG. J. Clin. Neurophysiol. 2001; 18(3):223-45.
Rahimi, et al. On the Effectiveness of Aluminum Foil Helmets: An Empirical Study. Available at http://people.csail.mit.edu/rahimi/helmet/. Accessed Mar. 2, 2006.
Robinson, et al. Steady States and Global Dynamics of Electrical Activity in the Cerebral Cortex. Phys. Rev. E. 1998; (58):3557-3571.
Rudrauf, et al. Frequency flows and the time-frequency dynamics of multivariate phase synchronization in brain signals. NeuroImage. 2005. (19 pages.).
Saab, et al. A system to detect the onset of epileptic seizures in scalp EEG. Clin. Neurophysiol, 2005; 116:427-442.
Sackellares et al. Computer-Assisted Seizure Detection Based on Quantitative Dynamical Measures. American Electroencephalographic Society Annual Meeting, Sep. 1994.
Sackellares et al. Dynamical Studies of Human Hippocampin Limbic Epilepsy. Neurology. 1995; 45, Suppl. 4, pp. A 404.
Sackellares et al. Epileptic Seizures as Neural Resetting Mechanisms. Epilepsia. 1997; vol. 38, Sup. 3.
Sackellares et al. Measurement of Chaos to Localize Seizure Onset. Epilepsia. 1989; 30(5):663.
Sackellares et al. Relationship Between Hippocampal Atrophy and Dynamical Measures of EEG in Depth Electrode Recordings. American Electroencephalographic Society Annual Meeting, Sep. 1995. pp. A105.
Sackellares et al.; Predictability analysis for an automated seizure prediction algorithm; Journal of Clinical Neurophysiology; vol. 23; No. 6; pp. 509-520; Dec. 2006.
Sackellares, J. C. Epilepsy—when chaos fails. In: chaos in the brain? Eds. K. Lehnertz & C.E. Elger. World Scientific. 2000 (22 pages).
Salant, et al. Prediction of epileptic seizures from two-channel EEG. Med. Biol. Eng. Comput. 1998; 36(5):549-56.
Schelter et al.; Testing statistical significance of multivariate time series analysis techniques for epileptic seizure prediction; Chaos: An Interdisciplinary Journal of Nonlinear Science; vol. 16; No. 013108; pp. 1-10; Jan. 2006.
Schelter, et al. Testing for directed influences among neural signals using partial directed coherence. J. Neurosci. Methods. 2006; 152(1-2):210-9.

(56) References Cited

OTHER PUBLICATIONS

Schindler, et al. EEG analysis with simulated neuronal cell models helps to detect pre-seizure changes. Clin. Neurophysiol. 2002; 113(4):604-14.
Schwartzkroin, P. Origins of the Epileptic State. Epilepsia. 1997; 38, supply. 8, pp. 853-858.
Sheridan, T. Humans and Automation. NY: John Wiley. 2002.
Shoeb et al. Patient-specific seizure detection. MIT Computer Science and Artificial Intelligence Laboratory. 2004; pp. 193-194.
Staba, et al. Quantitative analysis of high-frequency oscillations (80-500 Hz) recorded in human epileptic hippocampand entorhinal cortex. J. Neurophysiol. 2002; 88(4):1743-52.
Stefanski, et al. Using chaos synchronization to estimate the largest Lyapunov exponent of nonsmooth systems. Discrete Dynamics in Nature and Society. 2000; 4:207-215.
Subasi, et al. Classification of EEG signals using neural network and logistic regression. Computer Methods Programs Biomed. 2005; 78(2):87-99.
Szoka et al. Procedure for preparation of liposomes with large internal aqueospace and high capture volume by reverse phase evaporation. 1978. Proc. Natl Acad. Sci. USA. 75: 4194-4198.
Tass, et al. Detection of n: m Phase Locking from Noisy Data: Application to Magnetoencephalography. Physical Review Letters. 1998; 81(15):3291-3294.
Terry, et al. An improved algorithm for the detection of dynamical interdependence in bivariate time-series. Biol. Cybern. 2003; 88(2):129-36.
Tetzlaff, et al. Cellular neural networks (CNN) with linear weight functions for a prediction of epileptic seizures. Int''l. J. of Neural Systems. 2003; 13(6):489-498.
Theiler, et al. Testing for non-linearity in time series: the method of surrogate data. Physica D. 1992; 58:77-94.
Tsakalis, K. S. Prediction and control of epileptic seizures: Coupled oscillator models. Arizona State University. (Slide: 53 pages) (No date).
Van Drongelen, et al. Seizure anticipation in pediatric epilepsy: use of Kolmogorov entropy. Pediatr. Neurol. 2003; 29(3): 207-13.
Van Putten, M. Nearest neighbor phase synchronization as a measure to detect seizure activity from scalp EEG recordings. J. Clin. Neurophysiol. 2003; 20(5):320-5.
Venugopal, et al. A new approach towards predictability of epileptic seizures: KLT dimension. Biomed Sci. Instrum. 2003; 39:123-8.
Vonck, et al. Long-term amygdalohippocampal stimulation for refractory temporal lobe epilepsy. Ann. Neurol. 2002; 52(5):556-65.
Vonck, et al. Long-term deep brain stimulation for refractory temporal lobe epilepsy. Epilepsia. 2005; 46(Suppl 5):98-9.
Vonck, et al. Neurostimulation for refractory epilepsy. Acta. Neurol. Belg. 2003; 103(4):213-7.
Weiss, P. Seizure prelude found by chaos calculation. Science News. 1998; 153(20):326.
Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.
Widman, et al. Reduced signal complexity of intracellular recordings: a precursor for epileptiform activity? Brain Res. 1999; 836(1-2):156-63.
Winterhalder, et al. Sensitivity and specificity of coherence and phase synchronization analysis. (In Press) Phys. Lett. A. 2006.
Winterhalder, et al. The seizure prediction characteristic: a general framework to assess and compare seizure prediction methods. Epilepsy Behav. 2003; 4(3):318-25.
Wong et al.; A stochastic framework for evaluating seizure prediction algorithms using hiden markov models; Journal of Neurophysiology; vol. 97, No. 3; pp. 2525-2532; Oct. 4, 2006.
Yang et al.; Testing whether a prediction scheme is better than guess; Ch. 14 in Quantitative Neuroscience: Models, Algorithms, Diagnostics, and Therapeutic Applications; pp. 252-262; 2004.
Yang, et al. A supervised feature subset selection technique for multivariate time series. Available at http://infolab.usc.edu/DocsDemos/fsdm05.pdf. Accessed Mar. 2, 2006.
Yang, et al. CLe Ver: A feature subset selection technique for multivariate time series. T. B. Ho, D. Cheung, and H. Liu (Eds.): PAKDD. 2005; LNAI 3518: 516-522.
Yang, et al. Relation between Responsiveness to Neurotransmitters and Complexity of Epileptiform Activity in Rat Hippocampal CA1 Neurons. Epilepsia. 2002; 43(11):1330-1336.
Yatsenko, et al. Geometric Models, Fiber Bundles, and Biomedical Applications. Proceedings of Institute of Mathematics of NAS of Ukraine. 2004; 50 (Part 3):1518R1525.
Zaveri et al. Time-Frequency Analyses of Nonstationary Brain Signals. Electroencephalography and Clinical Neurophysiology. 1991; 79, pp. 28P-29P.
Zhang, et al. High-resolution EEG: cortical potential imaging of interictal spikes. Clin. Neurophysiol. 2003; 114(10):1963-73.
DiLorenzo, Daniel, U.S. Appl. No. 11/282,317 entitled "Closed-loop vagus nerve stimulation," filed Nov. 17, 2005.
Bland et al.; U.S. Appl. No. 12/180,996 entitled "Patient advisory device," filed Jul. 28, 2008.
Leyde et al.; U.S. Appl. No. 12/343,376 entitled "Systems and method for recording clinical manifestations of a seizure," filed Dec. 23, 2008.
Snyder et al; The statistics of a practical seizure warning system; Journal of Neural Engineering; vol. 5; pp. 392-401; 2008.
Higgins et al.; U.S. Appl. No. 13/026,961 entitled "Neurological monitoring and alerts," filed Feb. 14, 2011.
Harris et al.; U.S. Appl. No. 13/050,839 entitled "System and methods for analyzing seizure activity," filed Mar. 17, 2011.
Leyde et al.; U.S. Appl. No. 13/070,333 entitled "Communication Error Alerting in an Epilepsy Monitoring System," filed Mar. 23, 2011.
Leyde et al.; U.S. Appl. No. 13/070,357 entitled "Patient Entry Recording in an Epilepsy Monitoring System," filed Mar. 23, 2011.
Chen et al.; Clinical utility of video—EEG monitoring; Pediatric Neurology; vol. 12; No. 3; pp. 220-224; Apr. 1995.
DiLorenzo, Daniel; U.S. Appl. No. 12/774,550 entitled "Systems for Monitoring a Patient's Neurological Disease State," filed May 5, 2010.
Echauz et al.; U.S. Appl. No. 12/792,582 entitled "Processing for Multi-Channel Signals," filed Jun. 2, 2010.
Himes, David M.; U.S. Appl. No. 12/630,300 entitled "Universal Electrode Array for Monitoring Brain Activity," filed Dec. 3, 2009.
Himes et al.; U.S. Appl. No. 12/646,783 entitled "Brain State Analysis Based on Select Seizure Onset Characteristics and Clinical Manifestations," filed Dec. 23, 2009.
Echauz et al.; U.S. Appl. No. 12/649,098 entitled "Processing for Multi-Channel Signals," filed Dec. 29, 2009.
Floyd et al.; U.S. Appl. No. 12/685,543 entitled "Medical Lead Termination Sleeve for Implantable Medical Devices," filed Jan. 11, 2010.
Harris et al.; U.S. Appl. No. 12/691,650 entitled "Minimally invasive system for selecting patient-specific therapy parameters," filed Jan. 21, 2010.
Himes et al.; U.S. Appl. No. 12/716,132 entitled "Displaying and Manipulating Brain Function Data Including Enhanced Data Scrolling Functionality," filed Mar. 2, 2010.
Himes et al.; U.S. Appl. No. 12/716,147 entitled "Displaying and Manipulating Brain Function Data Including Filtering of Annotations," filed Mar. 2, 2010.
Rothman et al.; Local Cooling: a therapy for intractable neocortical epilepsy; Epilepsy Currents; vol. 3; No. 5; pp. 153-156; Sep./Oct. 2003.

\* cited by examiner

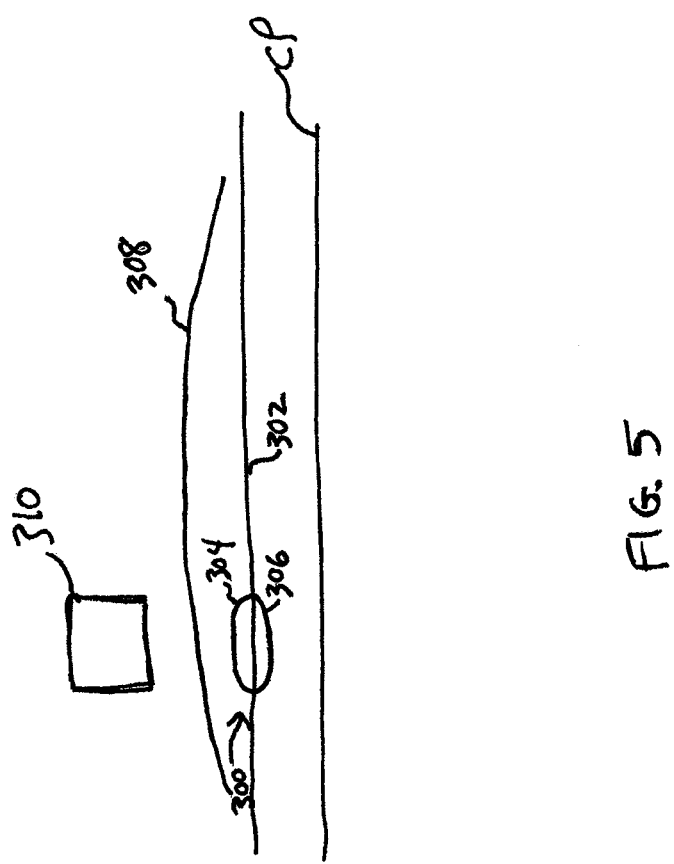

HOUSING FOR AN IMPLANTABLE MEDICAL DEVICE

CROSS REFERENCE TO RELATED APPLICATIONS

This application claims the benefit of U.S. Provisional Application No. 61/017,504, filed Dec. 28, 2007, which is incorporated in its entirety by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates to an electronic medical device for implanting into a living body, and more particularly to the structure and method of manufacture of the device's outer housing for the purposes of enhancing the device's transcutaneous electromagnetic coupling to extracorporeal systems for the transfer of energy and/or information via telemetry. Such implantable devices include, without limitation, pacemakers; defibrillators; drug delivery pumps; cochlear implants; brain activity monitoring/stimulation systems (such as for sleep apnea and other sleep disorders, migraine headaches, epilepsy, depression, Alzheimer's, Parkinson's Disease, essential tremor, dementia, bipolar spectrum disorders, attention deficit disorder, stroke, cardiac disease, diabetes, cancer, eating disorders, and the like); implantable diagnostic devices used to monitor a patient's neurological condition, to determine, e.g., the patient's real-time susceptibility to a seizure for a time period.

BACKGROUND OF THE INVENTION

Many implantable medical electronic devices utilize an internal source of electrical energy to power the device electronics for the purposes of, for example, diagnostics and/or therapy. Additionally, many implantable devices require such a significant amount of power that it is necessary to utilize transcutaneous energy transmission (TET) from an extracorporeal source to an implanted receiver which is connected to a rechargeable battery. To date, one of the more efficient recharging means employs an external transmission coil and an internal receiver coil which are inductively coupled. In this TET approach, the external primary transmission coil is energized with alternating current (AC), producing a time varying magnetic field that passes through the patient's skin and induces a corresponding electromotive force in the internal secondary receiving coil. The voltage induced across the receiving coil may then be rectified and used to power the implanted device and/or charge a battery or other charge storage device. Additionally, many medical electronic devices rely on noninvasive telemetry in order to allow data and control signals to be bi-directionally communicated between the implanted medical device and an external device or system. Such telemetry can be accomplished via a radio frequency (RF) coupled system using a transmitting antenna to a receiving antenna by way of a radiated carrier signal, or by using the power transfer coils for data transmission.

Electronic circuits and systems that are to be implanted in living organisms are hermetically packaged in a biocompatible material for the purposes of protecting the electronic circuitry from body fluids and protecting the organism from infection or other injury caused by the implanted materials. The most commonly used materials for implantable electronic devices are biocompatible metals, glass, and ceramics. Biocompatible metals include, for example without limitation, titanium, a titanium alloy, stainless steel, cobalt-chromium, platinum, niobium, tantalum, and various other possible alloys. Normally, metal enclosures consist of separate metal parts welded together to insure hermeticity. However, implant enclosures made of conductive metal present difficulties with respect to both transcutaneous energy transmission and telemetry. Specifically, the time varying magnetic charging field induces eddy currents within the metal housing and inhibits the magnetic flux as it passes through the case. With respect to RF telemetry from the implanted device to a receiver external to the patient, the metal case acts as a Faraday cage and tends to limit the rate of information transfer between the implanted device and the external system due to circulating eddy currents that absorb energy from the magnetic field and produce a magnetic field that opposes the incident magnetic field. The magnitude of the eddy currents is approximately proportional to the frequency of the AC magnetic field because the magnitude of the voltage induced within the conductive material is proportional to the time rate of change of magnetic flux as described in Faraday's Law, $E=-d\Phi/dt$, where E is the induced voltage and $\Phi$ is the magnetic flux impinging on the material. The carrier frequency for telemetry is limited by the amount of eddy current attenuation that the system can tolerate.

It is necessary to transmit significant amounts of power through the device case in order to recharge the device battery in a reasonable period of time. The implanted induction charging system typically uses a two-winding transformer with a non-ferrous (air) core. The energy transfer efficiency is approximately proportional to the number of turns in the transformer windings and the rate of change (frequency) of the alternating current, as follows:

$$e_2 = M\, di_1/dt + L_2\, di_2/dt$$

Where $e_2$ is the voltage induced across the secondary winding, M is the mutual inductance of the primary and secondary windings, $L_2$ is the inductance of the secondary winding and $di_1/dt$ and $di_2/dt$ are the time rate of change (frequency) of the primary and secondary currents.

Because the physical size of the implanted device limits the size and, hence, the inductance ($L_2$) of the receiving coil within the device, it is desirable to operate the inductive coupling system at the highest possible frequency in order to obtain the maximum coupling efficiency and energy transfer. Raising the operating frequency, however, increases the eddy current losses, so that the overall induction system efficiency is severely reduced. Additionally, such induced eddy currents create unwanted heat within the implantable enclosure.

A number of approaches have been proposed to address the limitations of induced eddy currents upon a metallic medical device enclosure with respect to TET and telemetry systems:

Ceramic Sleeve with a Metal Header. One approach is to utilize a deep drawn ceramic sleeve forming the majority of the enclosure body. The sleeve has a closed end, an open end for receiving electronic components and a metallic header for closing the open end (see U.S. Pat. No. 4,991,582.) Such a device, when implanted, has ceramic distal, proximal and side walls (relative to the skin) and an extracorporeal charging and/or telemetry device. This approach has, however, primarily been limited to small medical device enclosures (e.g., cochlear implants) due to the weight of the ceramic material. For larger devices such as an implantable pulse generator, the weight of the ceramic sleeve becomes a significant limitation due to the overall weight of the enclosure given the amount of ceramic used, the relatively large density of the ceramic, and the required large wall thickness (see also U.S. Pat. No. 6,411, 854).

Polymer Casing. Another approach is to avoid using both metal (problematic due to eddy currents) and ceramic (problematic due to weight) in favor of a biocompatible polymer material for the outer enclosure. This approach attempts to use epoxy to encapsulate the receiving coil, antenna, and a secondary enclosure and provide a hermetically sealed subhousing for the system electronics. The polymer and/or epoxy material does not, however, provide for a true hermetic seal, as eventually body fluids migrate through the material and degrade the receiving coil and antenna.

External Coil. In order to circumvent the problem of the metal housing material reducing the efficiency of the TET induction system efficiency, some devices have opted to place the receiving induction coil on the outside of the metal housing. This approach, however, increases both the size of the implant, the complexity of the surgical implant process, and the complexity of the device given the necessity for additional hermetic electrical feed-through connections between the secondary coil and the internal electronic circuitry. Additionally, the external coil would still have to be a biocompatible material as with the polymer casing approach above.

Thin Metal Window. U.S. Pat. No. 7,174,212 presents an approach for increasing the efficiency of high speed/high carrier frequency telemetry via the use of (1) a metallic housing having a thin metal telemetry window having a thickness on the order of 0.005 inches and/or (2) a metal alloy (e.g., titanium alloy) window having reduced electrical conductivity parameters. However, as the window material still is made of an electrically conductive material (although reduced in thickness), this solution is non-ideal as an RF telemetry signal and/or a magnetic field will still induce eddy currents thereby reducing the efficiency of the telemetry link.

Machined Grooves in Metal Casing. U.S. Pat. No. 5,913, 881 presents an approach for increasing the efficiency of high speed/high carrier frequency telemetry by creating grooved recesses arranged on either or both sides of the implanted housing wall to reduce the overall thickness of the wall and to create discontinuities along the wall surface in order to reduce the conductivity of the metal housing wall, thereby decreasing the induced eddy currents and providing increased telemetry efficiency.

Other hermetic housings for implantable medical devices are described in U.S. Pat. No. 4,785,827 and U.S. Pat. No. 5,876,424.

Improved medical device structures and methods of manufacture are needed to overcome at least the shortcomings stated above.

SUMMARY OF THE INVENTION

Described herein is a hermetically sealed implantable medical device housing having a construction permitting for efficient magnetic coupling and RF telemetry via a non-metal housing free path from the implantable device electronics to the remote charging and telemetry unit while also being relatively light weight. Additionally, this housing design allows for increased manufacturing efficiency and a more mechanically stable/robust housing to mount the internal electronic and mechanical components.

One aspect provides an implantable medical device having a first housing component comprising a first material mated to a second housing component comprising a second material. The first housing component may be a ceramic housing component (formed, e.g., from zirconium oxide, aluminum oxide and/or boron nitride), and the second housing component may be a metal housing component (formed, e.g., from platinum, niobium, titanium, tantalum and/or alloys of these metals) attached to the ceramic housing component to form a hermetically sealed enclosure. An electronic trans-housing magnetic flux component may be disposed within the enclosure. In some embodiments, the electronic trans-housing magnetic flux component includes a telemetry transmission coil, and in some embodiments, the electronic trans-housing magnetic flux component includes an magnetic flux energy receiver coil. Some embodiments also have a metal weld ring brazed onto the ceramic housing component and welded onto the metal housing component. The ceramic housing component may have a wall thickness between about 0.06 inches and about 0.30 inches, and the metal housing component may have a wall thickness between about 0.01 inches and about 0.10 inches. In some embodiments, the implant may also have an electrode connector within the enclosure communicating with an opening in the metal housing component; and a ceramic component surrounding the opening.

Another aspect provides an implantable medical device having a ceramic housing component (formed, e.g., from zirconium oxide, aluminum oxide and/or boron nitride); a metal housing component (formed, e.g., from platinum, niobium, titanium, tantalum and/or alloys of these metals); a circumferential sealing member attached to a periphery of the ceramic housing component and to a periphery of the metal housing component to form a hermetically sealed enclosure; and an electronic trans-housing magnetic flux component disposed within the enclosure. In some embodiments, the electronic trans-housing magnetic flux component includes a telemetry transmission coil, and in some embodiments, the electronic trans-housing magnetic flux component includes an magnetic flux energy receiver coil. The ceramic housing component may have a wall thickness between about 0.06 inches and about 0.30 inches, and the metal housing component may have a wall thickness between about 0.01 inches and about 0.10 inches. In some embodiments, the implant may also have an electrode connector disposed within the metal housing component, the electrode connector having a sealable opening communicating with the enclosure. The electrode connector may be made of ceramic.

Still another aspect provides an implantable medical device having a first metal housing component (formed, e.g., from platinum, niobium, titanium, tantalum and/or alloys of these metals); a second metal housing component, the second metal housing component forming an opening; a ceramic housing component (formed, e.g., from zirconium oxide, aluminum oxide and/or boron nitride) disposed in the opening, the first metal housing component, the second metal housing component and the ceramic housing component cooperating to form a hermetically sealed enclosure; and an electronic trans-housing magnetic flux component disposed within the enclosure. In some embodiments, the electronic trans-housing magnetic flux component includes a telemetry transmission coil, and in some embodiments, the electronic trans-housing magnetic flux component includes an magnetic flux energy receiver coil. The ceramic housing component may have a wall thickness between about 0.06 inches and about 0.30 inches, and the first metal housing component may have a wall thickness between about 0.01 inches and about 0.10 inches. In some embodiments, the implant may also have an electrode connector disposed within the first metal housing component, the electrode connector having a sealable opening communicating with the enclosure. The electrode connector may be made of ceramic.

Still another embodiment provides a clamshell type of housing having a pair of confronting concave components which when mated together form a perimeter parting line. This line forms a plane, which when implanted in the human body lies approximately parallel to the coronal plane. The distal concave component (relative to the patient's skin) is made of a biocompatible metal while the proximal concave component is made of a ceramic thereby allowing magnetic flux to pass through the proximal implant side to the extracorporeal charging device and/or telemetry unit.

In yet another embodiment, a metallic enclosure is constructed having a ceramic window located on the proximal implant side relative to the patient skin and lies approximately parallel to the coronal plane in the human body.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5 shows a cross-sectional view of an implanted medical device within a patient relative to the coronal plane of the patient.

DETAILED DESCRIPTION OF THE INVENTION

Figure 1:
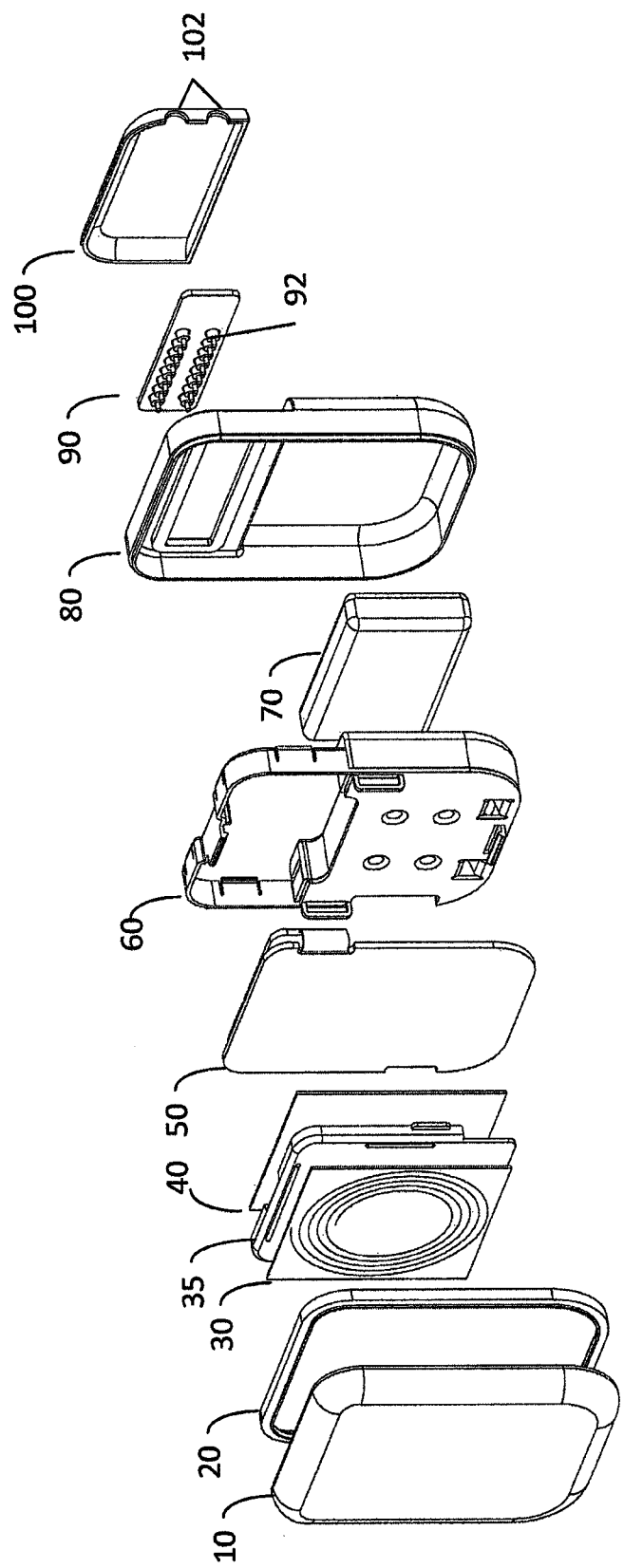
FIG. 1 is an exploded perspective view of an implantable medical device according to an embodiment of the invention.

FIG. 1 is an exploded perspective view of a hermetically sealed implantable medical device according to one embodiment of the invention. The medical device housing includes ceramic housing component 10 which is made of ceramic material such as, for example without limitation, zirconium oxide, yttrium stabilized zirconium oxide, aluminum oxide, boron nitride, or other suitable material. When implanted, ceramic component 10 is disposed proximate the patient's skin, i.e., it is disposed between the portion of the patient's skin where an extracorporeal charging and/or telecommunication device will be positioned and the implanted trans-housing magnetic flux component(s), such as an implanted telemetry coil or battery charger coil (see e.g., FIG. 5). The ceramic proximal housing component 10 therefore allows magnetic flux associated with inductive charging and/or radio frequency/inductive telemetry to efficiently pass through the hermetically sealed enclosure proximal face without inducing eddy currents.

In some embodiments the ceramic housing component has a wall thickness between about 0.03 inches and about 0.30 inches, and in some particular embodiments between about 0.06 inches and about 0.30 inches.

The implantable medical device also includes metal housing component 80 made of a biocompatible metal (such as platinum, niobium, titanium, tantalum, or an alloys of one or more of these metals) that cooperates with the ceramic housing component 10 to form a hermetic enclosure. In this embodiment, metal housing component 80 is attached to ceramic housing component 10 with weld ring 20 which is brazed onto the ceramic housing component and welded onto the metal housing component using techniques known in the art. Weld ring 20 is made of a biocompatible metal material such as, for example without limitation, platinum, niobium, titanium and tantalum, or any alloy of one or more of these metals. When implanted, metal housing component 80 is oriented distal to the portion of the implanted trans-housing magnetic flux component(s), i.e., not between the portion of the patient's skin where an extracorporeal charging and/or telecommunication device will be positioned and the implanted trans-housing magnetic flux component(s) (see e.g., FIG. 5).

In some embodiments the metal housing component has a wall thickness between about 0.01 inches and about 0.10 inches.

In this embodiment, ceramic plate 90 is brazed within an opening in the metal housing component 80 to allow implanted diagnostic and/or therapeutic electrodes to be connected into the hermetically sealed enclosure. Plate 90 has sealable ferrule connectors 92 through which electrode leads may pass from the enclosure to the exterior of the implant housing. Metal header 100 is used to support and cover the electrode feed-through ferrule connectors 92. Header 100 has one or more openings 102 which are configured to allow electrical leads to pass through the header from the enclosure to the exterior of the housing. When attached, header 100 cooperates with metal housing component 80 to complete the enclosure formed by the housing. Plate 90 may be formed from other biocompatible non-conductive materials as well.

The mechanical and electrical components of the implantable medical device are placed within the enclosure prior to connecting the housing components. In this illustrated embodiment, the medical device components include secondary coil 30 which is used for receiving transcutaneously transferred energy from an extracorporeal primary coil charging device. Exemplary external devices that can be used to transfer energy (and/or data) to the medical device housings described herein can be found in co-pending U.S. patent application Ser. No. 12/180,996, filed Jul. 28, 2008, which is hereby incorporated by reference herein. Coil 30 is shown as a planar winding made from conductive traces on a printed circuit board. Alternative embodiments include discrete wire windings either in a planar geometry or a coil/bobbin geometry. Such discrete wire windings have highly conductive properties and may include silver wire, copper wire, copper magnetic wire, Litz wire, woven wire, gold alloy, or other suitable materials known in the art. Located behind (i.e., distal to) the winding is magnetic flux shield/diverter 40 which serves to provide a lower reluctance magnetic return to the primary coil thereby increasing the transfer of energy as well as shielding implantable electronics 50 from the large magnetic fields. The magnetic material of flux shield 40 generally has a high magnetic permeability, and may be, for example without limitation, ferrite, Metglas® (Metglas Inc, Conway, S.C., U.S.A), Mµ metal (Mµ Shield Co., Manchester, N.H., U.S.A), Wave-X™ (ARC Technologies, Inc. Amesbury, Mass., U.S.A.), or other suitable material. Spacer 35, which in some embodiments is made of plastic, is disposed between coil 30 and magnetic flux shield/diverter 40 and serves to capture coil 30 and flux diverter 40 and maintain their spacing from electronics 50. In some embodiments spacer 35 is an internal frame (or chassis) that mechanically locates/protects several of the internal components. Spacer 35 may additionally facilitate manufacturing by offering a basis for a stand-alone subassembly. For example, charge coil 30, electronic components 50, and/or other components can be mechanically affixed to spacer element 35 prior to installation inside the titanium-ceramic housing.

The medical device implant electronics 50 are located on a board located behind (distal to) the magnetic flux shield/diverter 40. The medical device implant electronics 50 may, e.g., control therapy and/or diagnostic processes of the implant. For example, the implant electronics may include a rectifier and a charging circuit which allows a coupled AC voltage to be converted to a DC voltage in order to charge implantable rechargeable battery 70. The implant electronics may also include telemetry components to allow data and control signals to be bi-directionally communicated between the implanted medical device and an external device or system. This telemetry may be accomplished via an RF-coupled system using a transmitting antenna to a receiving antenna by way of a radiated carrier signal. Such antenna(s) within the implant may be located on the proximal side or below or above the magnetic shield 40 in order to insure the signals are not attenuated by the magnetic shield. An additional advantage of the distal placement of the metal housing component is the fact that this back conducting plate will enhance the projection of the radiating carrier signal towards the extracorporeal telemetry unit.

Behind, or distal to, electronics board 50 is compliant liner 60 which houses rechargeable power source 70. The rechargeable power source can be any of a variety of power sources including a chemically-based battery or a capacitor. Exemplary batteries include, without limitation, Lithium-ion (Li) and Li-polymer batteries which are examples of small and thin batteries. Alternative rechargeable batteries which may be used include, without limitation, lead-acid, Ni-iron, Ni-cadmium, Ni-Metal Hydride, Ni-zinc, Li-iron phosphate, Li-sulfur, Li-Nano Titanate, Zinc bromide, and other rechargeable batteries known in the art.

In this embodiment, when ceramic housing component 10 and metal housing component 80 are mated together by welding distal metal housing 80 to weld ring 20 and brazing weld ring 20 onto ceramic housing 10, the parting line between the two enclosure housings forms a plane. FIG. 5 is a cross-sectional top view showing an exemplary embodiment of implanted medical device 300 in which this plane 302, once the medical device is implanted in the human body, lies approximately parallel to the coronal plane "CP" of the human body. The proximal housing component 304 (e.g., ceramic housing component) faces outward towards the patient skin 308, while the distal housing component 306 (e.g., distal housing component) is distal relative to the proximal housing component. External device 310 is positioned adjacent the skin and can transmit energy (and/or receive data) to implanted medical device 300. In alternative embodiments, the medical device may be implanted within the patient at a location such that the plane formed by the parting line between two housing components is not parallel to the coronal plane. The plane will depend on where the medical device is implanted and for what purpose the medical device is implanted within the patient.

Additionally, the plane formed by the parting line between two housing components is not always generally parallel to the patient's skin. The plane may be offset at an angle from the general plane of the skin, as long as the medical device enclosure is implanted in such an orientation that an external device can transmit power and/or data through the ceramic housing component (and/or receive data therethrough).

This configuration provides for a light weight enclosure because the distal concave enclosure housing 80 is made of thin metal. This configuration also provides an enclosure which allows for the efficient transmission of magnetic flux to the extracorporeal charging device and telemetry unit via the proximal ceramic housing component 10.

Finally, the medical implant housing of this embodiment has additional advantages over a deep drawn ceramic implant housing having a metallic header. For example, this embodiment provides a simplified manufacturing processes as well as a more robust design. As illustrated in FIG. 1, the housing and the electronic and mechanical components are all amenable to top-down assembly processes as compared to the metal header deep drawn ceramic enclosure. Additionally, as the back (i.e., distal) side of the enclosure is metal, electronic and mechanical components can be mounted against the metallic housing component. In the deep drawn ceramic enclosure, on the other hand, all of the mechanical and electronic components are mounted to the metal header which presents a more challenging assembly and creates a long lever in which significant amount of moment of inertia may be created.

Figure 2:
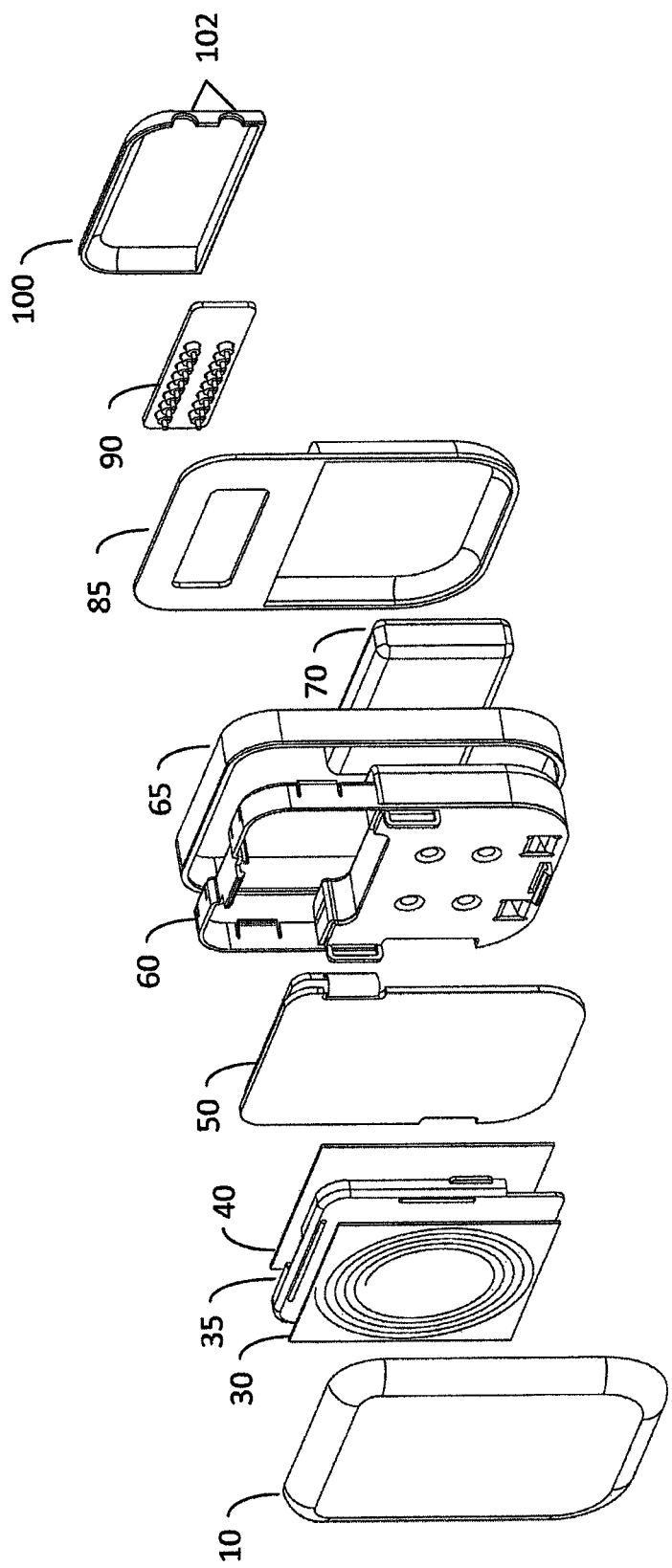
FIG. 2 is an exploded perspective view of an implantable medical device according to another embodiment of the invention.

FIG. 2 illustrates an alternative embodiment of the medical device housing shown in FIG. 1 that reduces or eliminates the concavity of the housing components. Wide metal band 65 around the outer perimeter of the housing spans the distance between the edge of ceramic housing component 10 and metal housing component 85. Band 65 cooperates with housing components 10, 85 and 100 to form a hermetic enclosure for the implant's components. This embodiment may permit the housing to be lighter due to a reduction in the amount of ceramic used to form the housing.

Figure 3:
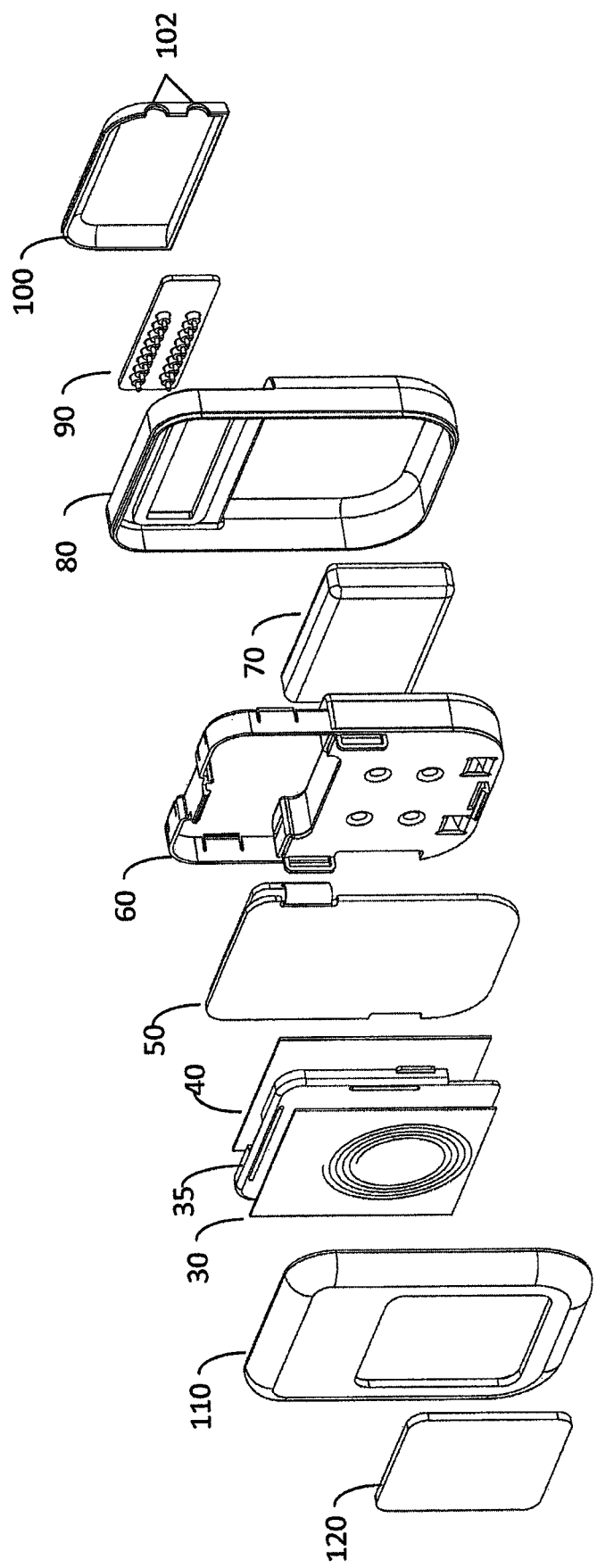
FIG. 3 is an exploded perspective view of an implantable medical device according to yet another embodiment of the invention.

FIG. 3 illustrates an alternative embodiment which represents a lighter weight device, in which proximal ceramic housing 10 of FIG. 1 is replaced with proximal biocompatible metal housing component 110. A ceramic window 120 is disposed in an opening in the metal housing component 110 which allows for the magnetic flux associated with inductively coupled charging and/or radio frequency telemetry to efficiently pass through the hermetically sealed enclosure proximal face without inducing eddy currents. The ceramic window 120 can be brazed onto the proximal biocompatible metal housing 110 prior to the installation of the implant electronics and hardware 30, 40, 50, 60 and 70. Next, the proximal metal housing component 110, which is coupled to ceramic window 120, and the distal metal housing component 80 are welded together. Many of the other elements of the medical device described in alternative embodiments herein can be incorporated into the embodiment shown in FIG. 3.

When the medical device from FIG. 3 is implanted in a patient, the proximal metal housing and ceramic window assembly are disposed closer to the skin than the distal housing component (as is proximal portion 304 shown in FIG. 5).

Figure 4:
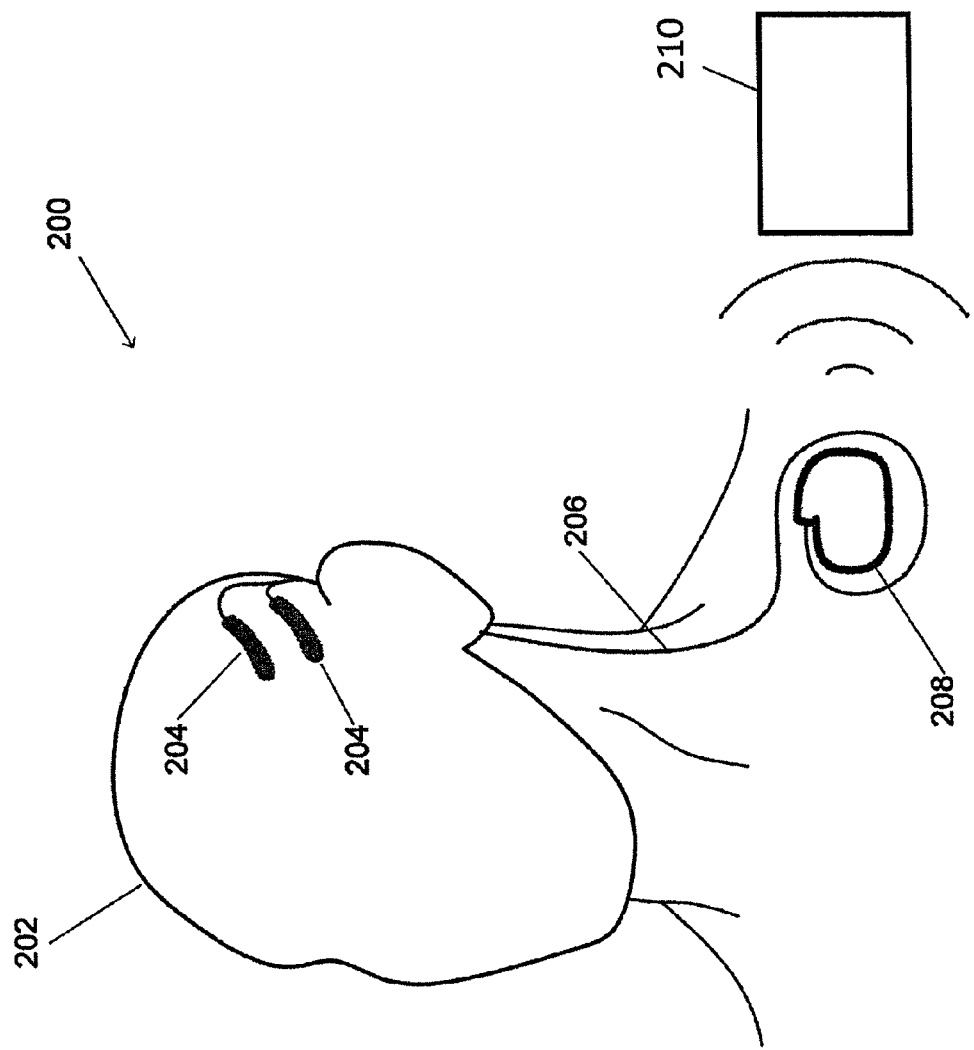
FIG. 4 shows the implantable medical device of FIGS. 1, 2 or 3 implanted in a patient.

FIG. 4 illustrates exemplary implantable medical device 208 located in the patient 200. Electronic lead 206 is attached to the medical device and attached to electrode arrays 204. In this example the electrode arrays 204 are implanted intracranially within head 202 and the cable(s) 206 is tunneled beneath the skin through the neck to the implanted medical device 208 that is implanted in a subclavicular cavity of the subject. Note however, that FIG. 4 is only shown as an example and the medical device implant is not limited to the subclavicular cavity, as it could be also located intracranially or any other place within the body. Similarly, the medical device is not limited to requiring electrodes placement within the intracranial cavity or requiring such electrodes at all.

An extracorporeal device 210 may be used as described herein to transfer energy and/or information via telemetry to device 208 across the patient's skin. To that end, device 208 is oriented within the patient so that a ceramic housing component is closer to the skin where extracorporeal device is positioned than is a metal housing component.

What is claimed is:

1. An implantable medical device comprising:
   a housing comprising a front side and an opposing back side defining an interior chamber disposed between the front and back sides, wherein the front side comprises a substantially-planar metal portion and an opening passing through the front side to communicate with the interior chamber;
   a ceramic window disposed in the opening;
   a printed circuit board disposed in the interior chamber and comprising electronic components positioned between the substantially-planar metal portion and the back side; and
   an electronic trans-housing magnetic flux component disposed within the interior chamber between the ceramic window and the back side, said magnetic flux component being configured to be magnetically coupled to an external flux component via a magnetic field passing through the ceramic window.

2. The implantable medical device of claim 1, wherein the electronic trans-housing magnetic flux component comprises a conductive trace formed on a printed circuit board.

3. The implantable medical device of claim 1, wherein the electronic trans-housing magnetic flux component further comprises a conductive wire winding.

4. The implantable medical device of claim 1, further comprising:
   a rechargeable battery disposed in the interior chamber and operatively coupled to the electronic trans-housing magnetic flux component.

5. The implantable medical device of claim 1, wherein the ceramic window is brazed to the opening of the front side.

6. The implantable medical device of claim 1, wherein the ceramic window includes a ceramic planar surface that is co-planar with the substantially-planar metal portion.

7. The implantable medical device of claim 1, wherein the front side is welded to the back side to define a peripheral side of the housing having a peripheral side surface that is orthogonal to the substantially-planar metal portion of the front side.

8. The implantable medical device of claim 1, wherein the back side comprises a substantially-planar metal portion disposed in a parallel orientation relative to the substantially-planar metal portion of the front side.

9. The implantable medical device of claim 1, wherein the magnetic flux component is disposed adjacent to the ceramic window.

10. The implantable medical device of claim 1, wherein the ceramic window comprises zirconium oxide, aluminum oxide, or boron nitride.

11. The implantable medical device of claim 1, wherein the ceramic window is formed from zirconium oxide and has a wall thickness between about 0.06 inches and about 0.30 inches.

12. The implantable medical device of claim 1, wherein the metal portion of the front side comprises platinum, niobium, titanium, tantalum, or an alloy of two or more of platinum, niobium, titanium, and tantalum.

13. The implantable medical device of claim 1, wherein the electronic components comprise a telemetry unit configured to receive inductive telemetry signals via the electronic trans-housing magnetic flux component.

14. The implantable medical device of claim 1, further comprising electronics disposed within the interior chamber adapted to control stimulation therapy.

15. An implantable medical device configured to receive energy from a primary coil disposed at a position external to the medical device, the device comprising:
   a metal housing component defining an interior chamber and having a metal opening edge defining an opening communicating with the interior chamber;
   a secondary coil; and
   a printed circuit board supporting the secondary coil disposed within the interior chamber to position the secondary coil adjacent to the opening to receive energy from the primary coil when the primary coil is disposed at the position external to the medical device,
   wherein a portion of the printed circuit board supporting the secondary coil fully occludes the opening as viewed from the position external to the medical device.

16. The implantable medical device of claim 15, further comprising:
   a ceramic housing component having a ceramic peripheral edge disposed to engage the metal opening edge, the metal housing component and the ceramic housing component together defining the interior chamber.

17. The implantable medical device of claim 15, wherein the secondary coil comprises a conductive trace formed on the printed circuit board.

18. The implantable medical device of claim 15, further comprising electronics disposed within the interior chamber adapted to control stimulation therapy.

19. An implantable medical device configured to receive energy from a primary coil, the device comprising:
   a secondary coil configured to receive energy from the primary coil;
   a housing defining an interior chamber, the housing having a first side and an opposing second side, the first side configured to face the primary coil when the primary coil and the secondary coil are in an aligned orientation suitable for the transmission of the energy from the primary coil to the secondary coil, the first side including a first metal portion and a second ceramic portion;
   a printed circuit board disposed in the interior chamber directly adjacent to the first metal portion; and
   the secondary coil disposed in the interior chamber directly adjacent to the second ceramic portion.

20. The implantable medical device of claim 19, further comprising:
   electronics disposed within the interior chamber adapted to control stimulation therapy.

21. The implantable medical device of claim 19, wherein the secondary coil is mounted on the printed circuit board.

22. The implantable medical device of claim 19, wherein the first metal portion defines an opening within the first metal portion, and wherein the second ceramic portion is disposed within the opening of the first metal portion.

23. The implantable medical device of claim 22, wherein the secondary coil is mounted on the printed circuit board and configured to be magnetically coupled to the primary coil via a magnetic field passing through the second ceramic portion.

* * * * *